United States Patent [19]
Keenan

[11] Patent Number: 5,643,928
[45] Date of Patent: Jul. 1, 1997

[54] HUMAN BODY WEIGHT MANAGEMENT

[75] Inventor: Robert M. Keenan, Baltimore, Md.

[73] Assignee: Pharmaco Behavioral Associates, Inc., Minneapolis, Minn.

[21] Appl. No.: 964,277

[22] Filed: Oct. 21, 1992

[51] Int. Cl.$^6$ ............................................. A61K 31/44
[52] U.S. Cl. .................................................. 514/343
[58] Field of Search ...................................... 514/343

[56] References Cited

U.S. PATENT DOCUMENTS

| | | | |
|---|---|---|---|
| 3,048,520 | 8/1962 | McKennis et al. | 167/65 |
| 3,867,519 | 2/1975 | Michaels . | |
| 3,870,791 | 3/1975 | Haddad et al. . | |
| 3,870,794 | 3/1975 | Hutchinson et al. | 424/264 |
| 4,051,842 | 10/1977 | Hazel et al. . | |
| 4,136,177 | 1/1979 | Lin et al. . | |
| 4,140,122 | 2/1979 | Kuhl et al. . | |
| 4,255,415 | 3/1981 | Chrai et al. . | |
| 4,383,529 | 5/1983 | Webster . | |
| 4,621,074 | 11/1986 | Bourne . | |
| 4,668,506 | 5/1987 | Bawa . | |
| 4,713,244 | 12/1987 | Bawa et al. . | |
| 4,788,063 | 11/1988 | Fisher et al. . | |
| 4,931,279 | 6/1990 | Bawa et al. . | |
| 4,946,853 | 8/1990 | Bannon et al. | 514/343 |
| 5,298,257 | 3/1994 | Bannon et al. | 514/343 |

FOREIGN PATENT DOCUMENTS

93/23045  11/1993  WIPO .

OTHER PUBLICATIONS

Cynthia S. Pomerleau et al., "The Female Weight–Control Smoker: A Profile", *J. Substance Abuse*, 5, 391, (1993).

Raymond Niaura et al., "Increased Saliva Cotinine Concentrations in Smokers During Rapid Weight Loss," *J. Consult. Clin. Psychol.*, 60, 985, (1992).

Ovide F. Pomerleau et al., "Effects of Fluoxetine on Weight Gain and Food Intake in Smokers Who Reduce Nicotine Intake," *Psychoneuroendocrinology*, 16, 433 (1991).

M. E. Carroll et al., "Nicotine Dependence in Rats," *Life Sciences*, 45, 1381–1388 (1989).

W. G. Frankenberg et al., "The chemistry of tobacco fermentation. I. Conversion of the alkaloids. D. Identification of cotinine in fermented leaves," *J. Am. Chem. Soc.*, 79, 149–151 (1957).

E. J. LaVoie et al., "Evaluation of the effects of cotinine and nicotine–N'–oxides in the development of tumors in rats initiated with N–[4–(5–nitro–2–furyl)–2–thiazoyl]formamide," *J. Nat. Cancer Institute*, 75, 1075–1081 (1985).

R. C. O'Neill, "Tobacco products containing nicotine antagonists," *Chemical Abstracts*, 55, 16920 (1961).

M. Rosa et al., "How the steady–state cotinine concentration in cigarette smokers is directly related to nicotine intake," *Clin. Pharmacol. Ther.*, 52, 324–329 (Sep. 1992).

R. Barbieri et al, "Nicotine, Cotinine and Anabasine Inhibit Aromatase in Human Trophoblast in Vitro", *J. Clin. J. Steroid Invest.*, 77:1727–1733 (1986).

R. Barbieri et al, "Nicotine, Cotinine and Anabasine on Rat Adrenal 11B–hydroxylase and 21–hydroxylase", *J. Steroid Biochem.*, 28: 25–28 (1987).

R. Barbieri, et al, "Cotinine and Nicotine Inhibit Human Fetal Adrenal 11B–hydroxylase", *Journal of Clinical Endocrinology and Metabolism*, 69:1221–1224 (1989).

N. Benowitz et al, "Cotinine Disposition and Effects", *Clin. Pharmacol. Ther.*, 34:604–611 (1983).

N. Benowitz et al, "Inverse Relation Between Serum Cotinine Concentration and Blood Pressure in Cigarette Smokers", *Circulation*, 80:1309–1312 (1989).

J. Borzelleca et al, "Studies on the Respiratory and Cardiovascular Effects of (–)–Cotinine", *J. Pharm. Exper. Therapeutics*, 137:313–318 (1962).

K. Bauman et al, "Validity of Self–Reports of Smokeless Tobacco Use and Validity of Cotinine as an Indicator of Cigarette Smoking", *The American Journal of Epidemiology*, 130:327–337 (1989).

E. Bowman et al, "(–)–Cotinine", *Biochemical Preparations*, 10:36–39 (1963).

E. Bowman et al, "Disposition and Fate of (–)–Cotinine in the Mouse", *The Journal of Pharmacology and Experimental Therapeutics*, 143:301–308 (1963).

E. Bowman et al, "Studies on the Metabolism of (–)–Cotinine in the Human", *J. Pharmacol. Exp. Ther.*, 135:306–311 (1962).

R. Chahine et al, "The in Vitro Effects of Nicotine and Cotinine on Prostacyclin and Thromboxane Biosynthesis", *Prostaglandins, Leukotrienes, and Essential Fatty Acids*, 40:261–266 (1990).

M. Curvall et al, "Simulation and Evaluation of Nicotine Intake During Passive Smoking: Cotinine Measurements in Body Fluids of Nonsmokers Given Intravenous Infusions of Nicotine", *Clinical Pharmacol Therapy*, 47:42–49 (1990).

M. Curvall et al, "The Pharmacokinetics of Cotinine in Plasma and Saliva from Non–Smoking Healthy Volunteers", *The European Journal of Clinical Pharmacology*, 38:281–287 (1990).

E. Di Giusto et al, "Some Properties of Saliva Cotinine Measurements in Indicating Exposure to Tobacco Smoking", *The American Journal of Public Health*, 76:1245–1246 (1986).

P. DeSchepper et al, "Kinetics of Cotinine After Oral and Intravenous Administration to Man", *The European Journal of Clinical Pharmacology*, 31:583–588 (1987).

J. Gabrielsson et al, "Constant–Rate Infusion of Nicotine and Cotinine. I. A Physiological Pharmacokinetic Analysis of the Cotinine Disposition, and Effects on Clearance and Distribution in the Rat", *The Journal of Pharmacokinetics and Biopharmaceutics* 15:583–599 (1987).

(List continued on next page.)

Primary Examiner—Raymond Henley, III
Attorney, Agent, or Firm—Schwegman, Lundberg, Woessner & Kluth, P.A.

[57] ABSTRACT

A therapeutic method and article of manufacture to manage human body weight with the use of cotinine or pharmaceutically acceptable salt thereof.

11 Claims, No Drawings

OTHER PUBLICATIONS

R. Galeazzi et al, "Steady-Stroke Concentration of Cotinine as a Measure of Nicotine–Intake by Smokers", *The European Journal of Clinical Pharmcology*, 28:301–304 (1985).

D. Glenn et al, "Synthesis and Mass Spectrometry of Some Structurally Related Nicotinoids", *The Journal of Organic Chemistry*, 43:2860–2870 (1978).

S. Goldberg et al, "Nicotine and Some Related Compounds: Effects on Schedule–Controlled Behavior and Discriminative Properties in Rats", *Psychopharmacology*, 97:295–302 (1989).

N. Heimstra, "The Effects of Smoking on Mood Change". (1986).

R. Hutchinson et al, "Effects of Nicotine on Avoidance, Conditioned Suppression and Aggression Response Measures in Animals and Man", 171–196. (1989).

J. Idle, "Titrating Exposure to Tobacco Smoke Using Cotinine–A Minefield of Misunderstanding", *The Journal of Clinical Epidemiol*, 43:313–317 (1990).

P. Jacob et al, "Disposition Kinetics of Nicotine and Cotinine Enantiomers in Rabbis and Beagle Dogs", *The Journal of Pharmaceutical Sciences*, 77:396–400 (1988).

L. Jarczyk et al, "Serum and Saliva Concentrations of Cotinine in Smokers and Passive Smokers", *The Journal of Clinical Chemical Biochemistry*, 27:230–231 (1989).

M. Jarvis et al, "Biochemical Markers of Smoke Absorption and Self Reported Exposure to Passive Smoking", *The Journal of Epidemiology and Community Health*, 38:335–339 (1984).

J. Jordanov, "Cotinine Concentrations in Amniotic Fluid and Urine of Smoking, Passive Smoking and Non–Smoking Pregnant Women at Term and in the Urine of Their Neonates on 1st Dat of Life", *The European Journal of Pediatrics*, 149:734–737 (1990).

K. Kim et al, "Effects of Some Nicotine Metabolites and Related Compounds on Isolated Smooth Muscle", *The Journal of Pharmacology and Experimental Therapeutics*, 161:59–69 (1968).

B. Kuo et al, "Influence of Nicotine and Cotinine on the Expression of Plasminogen Activator Activity in Bovine Aortic Endothelial Cells", *Thrombosis and Haemostasis*, 61:70–76 (1989).

G. Kyerematen et al, "Disposition of Nicotine and Eight Metabolites in Smokers and Nonsmokers: Identification in Smokers of Two Metabolites That are Longer Lived Than Nicotine", *Clinical Pharmacol Ther.*, 48:641–651 (1990).

W. Luck et al, "Extent of Nicotine and Cotinine Transfer to the Human Fetus, Placenta and Amniotic Fluid of Smoking Mothers", *Dev. Pharmacol. Ther.*, 8:384–395 (1985).

C. Lynch et al, "Spontaneous Cigarette Brand Switching: Consequences for Nicotine and Carbon Monoxide Exposure", *The American Journal of Public Health*, 78:1191–1194 (1987).

H. McKennis et al, "Demethylation of Cotinine in Vivo", *Demethylation of Cotinine in Vivo*, 81:3951–3954 (1959).

H. McKennis et al, "Alternate Routes in the Metabolic Degradation of the Pyrrolidine Ring of Nicotine", *The Journal of Biological Chemistry*, 239:3990–3996 (1964).

A. Meikle et al, "Nicotine and Cotinine Effects on 3 Alpha Hydroxysteroid Dehydrogenase in Canine Prostate", *Life Sciences*, 43:1845–1850 (1988).

A. McNeill et al, "Saliva Cotinine as an Indicator of Cigarette Smoking in Adolescents", *The British Journal of Addiction*, 82:1355–1360 (1987).

M. Noland et al, "Saliva Cotinine and Thiocyanate: Chemical Indicators of Smokeless Tobacco and Cigarette Use in Adolescents", *The Journal of Behavioral Medicine*, 11:423–433 (1988).

M. Risner et al, "Effects of Nicotine, Cocaine and Some of Thier Metabolites on Schedule–Controlled Responding by Beagle Dogs and Squirrel Monkeys", *The Journal of Pharmacology and Experimental Therapeutics*, 234:113–119 (1985).

Rylander et al, "Exposure to Environmental Tobacco Smoke and Urinary Excretion of Cotinine and Nicotine in Children", *Acta Poediatr Scand*, 78:449–450 (1989).

I. Sasson et al, "Cigarette Smoking and Neoplasia of the Uterine Cervix: Smoke Constituents in Cervical Mucus", *The New England Journal of Medicine*, 312:315–316 (1985).

G. Scherer et al, "Pharmacokinetics of Nicotine, Cotinine and 3'–Hydroxycotinine in Cigarette Smokers", *Klin Wochenschr*, 66:5–11 (1988).

S. Schwartz et al, "Studies on the Degradation of the Pyrrolidine Ring of (–)–Nicotine in Vivo", *The Journal of Biological Chemistry* 238:1807–1812 (1963).

D. Sepkovic et al, "Biomedical Applications of Cotinine Quantitation in Smoking Related Research", *Public Health Briefs, The American Journal of Public Health*, 75:663–665 (1985).

*Surgeon General*, "The Health Consequences of Smoking—Nicotine Addiction", 197–208 (1988).

B. Testa et al, "Circular Dichroic Determination of the Preferred Conformation of Nicotine and Related Chiral Alkaloids in Aqueous Solution", *Molecular Pharmacology*, 9:10–16 (1973).

S. Thompson et al, "Relation of Urinary Cotinine Concentrations to Cigarette Smoking and to Exposure to Other People's Smoke", *Thorax*, 45:356–361 (1990).

H. Van Vunkis et al, "Decreased Serum Cotinine Levels in Smokers of Both Tobacco and Marijuana as Compared With Smokers of Tobacco Only", *Pharmacology Biochemistry & Behavior*, 30:895–898 (1988).

L. Wagenknecht et al, "Racial Differences in Serum Cotinine Levels Among Smokers in the Coronary Artery Risk Development in (Young) Adults Study", *The American Journal of Public Health*, 80:1053–1056 (1990).

K. Yamamoto et al, "Nicotine–Induced Eeg and Behavioral Arousal", *Int. J. Neuropharamacol*, 4:359–373 (1965).

J. Yeh et al, "Nicotine and Cotinine Inhibit Rat Testis Androgen Biosynthesis in Vitro", *J. Steroid Biochem*, 33:627–630 (1989).

HUMAN BODY WEIGHT MANAGEMENT

FIELD OF THE INVENTION

The invention relates to therapeutic methods and articles of manufacture to manage human body weight with use of cotinine or pharmaceutically acceptable salt thereof. The invention includes methods and articles of manufacture using cotinine or pharmaceutically acceptable salt thereof to manage human body weight in nicotine-abstinent, and nicotine-naive humans.

BACKGROUND OF THE INVENTION

Tobacco use in the United States is responsible for more than 400,000 deaths per year due to many types of cancer and cardiovascular disease (See, Office of Smoking and Health, *The Health Consequences of Smoking: Nicotine Addition, A Report to the Surgeon General*, U.S. Government Printing Office, Washington, D.C., DHHS Publication Number (CDC) 88-8406 (1988)). Despite the grave consequences of tobacco use, the vast majority of tobacco users are unable to abstain from nicotine use for any extended period of time. One reason for this inability to abstain from nicotine use is the weight gain experienced by most tobacco users in the post-cessation period, with this being especially true for female cigarette smokers.

The relationship between tobacco use and decreased body weight has been known for more than 100 years. It has been well established that smokers weight less than non-smokers. Recent research has shown that nicotine is the substance responsible for the decreased body weight of tobacco users (See, *Chapter on Nicotine Dependence*, The National Institute on Drug Abuse's Fourth Triennial Report to Congress, In Press). Two major factors related to nicotine use cessation are responsible for weight gain in the post-tobacco cessation period including 1) decreased metabolism and/or 2) increased dietary intake. Conversely, it must be the case that nicotine use results in increased metabolism and/or increased dietary intake. In humans, intravenous nicotine infusion was shown to modestly increase the resting metabolic rate (6.5%) of smokers and non-smokers similarly. Also, in smokers and non-smokers alike, nasal nicotine solution insufflation significantly reduced the perceived taste intensity of dietary "fat", but not "sweets". From this, it appears that nicotine acts to decrease body weight through decreased calorie intake (i.e., appetite suppression) and increased metabolism. The mechanism for the observed appetite suppression is likely related to the increased serotonergic activity within the hypothalamus of the brain.

In an attempt to reduce post-cessation weight gain and achieve long-term tobacco cessation success, the affects of nicotine replacement (nicotine gum) on post-cessation weight gain were examined over a ten week post-cessation period. Nicotine gum when compared to placebo was shown to reduce the weight gained in the post-cessation period by approximately 50 percent (3.8 versus 7.8 pounds, respectively), and the magnitude of this beneficial effect was related to the amount of nicotine gum used. Similarly, it was found that nicotine gum use by abstinent cigarette smokers reduced the frequency and severity of self-reported "Hunger" scores and self-reported eating over the first month of nicotine abstinence. Increases in self-reported measures of hunger are likely related to increased weight gain in the post-cessation period (See, chapter on *Nicotine Dependence*, The National Institute on Drug Abuse's Fourth Triennial Report to Congress, In Press). As a result of the above findings, the use of an appetite suppressant, therefore, should prevent post-cessation weight gain in nicotine-experienced individuals.

Past cessation intervention strategies to reduce weight gain during smoking cessation have been attempted. The use of phenylpropanolamine gum, an appetite suppressant, was able to prevent weight gain in female cigarette smokers during two weeks of abstinence. In cigarette smokers attempting to quit, fluoxetine, a serotonergic agonist, was able to prevent the weight gain associated with cessation, as well as inducing decreased caloric intake during a test situation (See, chapter on *Nicotine Dependence*, The National Institute On Drug Abuse's Fourth Triennial Report to Congress, In Press). As a result, it appears that the use of an appetite suppressant during tobacco use cessation will reduce post-cessation weight gain and increase abstinence success.

Presently, while nicotine appears to act as an appetite suppressant through serotonergic mechanism and is partially effective in preventing the weight gain associated with tobacco use cessation in nicotine-experienced individuals and/or is able to increase metabolism and decrease caloric intake in nicotine-naive individuals, nicotine delivered through various forms of approved nicotine pharmacotherapies is toxic and not recommended for long-term use due to its adverse health effects and abuse potential due to nicotine's addicting nature.

SUMMARY OF THE INVENTION

The present invention provides a therapeutic method to (a) suppress appetite and/or prevent weight gain and/or induce weight loss in nicotine-experienced and/or nicotine-abstinent individuals during the post-tobacco use cessation period, or (b) suppress appetite and/or prevent weight gain and/or reduce body weight in nicotine-naive individuals comprising administering to a human in need of such treatment, i.e., a nicotine-experienced tobacco user or overweight person who does not engage in tobacco use, an amount of cotinine or a pharmaceutically acceptable salt thereof, in an amount effective to significantly suppress appetite and/or prevent weight gain and/or induce weight loss. The present method is effective for short-term appetite suppression and/or induction of weight loss and/or to maintain tobacco abstinence by preventing weight gain for extended periods of time.

The present invention is exemplified by a research study in which (−)-cotinine base was intravenously administered in a double-blind placebo-controlled manner to cigarette smokers. The cotinine administration when compared to placebo caused a decrease in self-reported ratings of "hunger" over a two hour period post-injection.

While it is known that nicotine is able to increase metabolism and/or decrease caloric intake in nicotine-experienced and nicotine-naive individuals, cotinine has a similar spectrum of pharmacologic activity to nicotine with cotinine being less potent that nicotine. Therefore, cotinine should act as an appetite suppressant in the same manner as nicotine.

Cotinine has many qualities which can enhance its value as an appetite suppressant in nicotine-experienced and/or nicotine-naive individuals. Cotinine has a long terminal half-life, complete oral bioavailability, minimal cardiovascular effect, low potential for abuse and has not been reported to be harmful even at very high doses in many species including man. Due to cotinine's minimal cardiovascular effect, cotinine should be able to be used in the immediate post-tobacco use cessation period in combination with currently existing and/or future nicotine replacement therapies.

The present invention also provides an article of manufacture comprising packaging material, such as a box, bottle, tube, sprayer, insufflator, intravenous (i.v.) bag, envelope and the like; and at least one unit dosage form of a pharmaceutical agent contained within said packaging material, wherein said pharmaceutical compound comprises cotinine or a pharmaceutically acceptable salt thereof in an amount effective to induce appetite suppression and/or prevent of weight gain and/or weight loss in nicotine-experienced and/or nicotine-naive individuals, and wherein said packaging material includes instruction means which indicate that said cotinine or said pharmaceutically acceptable salt thereof can be used for appetite suppression and/or prevention of weight gain and/or weight loss in nicotine-experienced and/or nicotine-naive individuals. Suitable instruction means include printed labels, printed package inserts, tags, cassette tapes, and the like.

DETAILED DESCRIPTION OF THE INVENTION

Cotinine

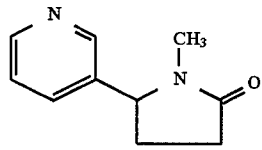

Cotinine (1-methyl-5-(3-pyridinyl)-2-pyrrolidinone) has the formula shown above;

The physiologically active form is the (−)-isomer, so as used herein, the term "cotinine" includes (−)-cotinine, or the racemic form, (+/−)-cotinine. The free base, depicted above, can be employed in the practice of the invention, as can the pharmaceutically acceptable salts thereof. These include the amine-acid addition salts of nontoxic organic acid or inorganic acids, such as the tartarate, fumarate ("scotine"), citrate, maleate, malate, hydrobromide, hydrochloride, sulfate, phosphate and the like. For example, see F. Vaitekunas, *J. Amer. Chem. Soc.*, 79, 149 (1957). E. R. Bowman et al., in *J. Pharmacol. Exp. Ther.*, 135, 306 (1962) report the preparation of (−)-cotinine free base from (−)-cotinine fumarate is described by N. L. Benowitz et al., *Clin. Pharmacol. Ther.*, 34, 604 (1983).

Cotinine is the major metabolite of nicotine which accumulates in the body as a result of nicotine exposure and has previously been believed to be pharmacologically inactive. For example, see N. L. Benowitz, "The use of biologic fluid samples in assessing tobacco smoke consumption", in *Measurement in the Analysis and Treatment of Smoking Behavior*, J. Grabowski et al. eds., NIDA Research Monograph No. 48, UPHS, ADAMHA (1983). In contrast to nicotine, cotinine has a relatively long terminal elimination half-life (two versus sixteen hours, respectively). Due to this pharmacological characteristic, cotinine has become the principally used objective biochemical marker of nicotine exposure in cigarette smoking and/or cessation-related research paradigms.

While cotinine is a well-known metabolite of nicotine and is routinely measured in many laboratories, no systematic investigation (using a double-blind placebo-controlled methodology) of the physiological and subjective effects produced by intravenous cotinine administration when compared to placebo has been performed in humans. K. I. Yamamoto et al., *International J. Neuropharmacol.*, 4, 359 (1965) reported that intravenous cotinine produced increases in EEG activity and behavioral arousal in cats with only a slight decrease in blood pressure. In squirrel monkeys, intramuscular cotinine injections increased rates of responding on fixed interval schedules of reinforcement over a wide range of doses (M. E. Risner et al. *J. Pharmacol. Exp. Ther.*, 234, 113 (1985); S. R. Goldberg et al., *Psychopharmacology*, 97, 295 (1989)). These findings, taken together, suggest that cotinine acts as a psychomotor stimulant. However, the pharmacologic mechanism of action has yet to be determined.

In two recent human studies, the pharmacokinetic profiles of intravenous and orally administered cotinine were examined without emphasis on measuring the subjective and/or physiological changes induced by this compound (N. L. Benowtiz et al., *Clin. Pharmacol. Therapeutics*, 34, 604 (1983); P. J. DeSchepper et al., *Eur. J. Pharmacal.*, 31, 583 (1987)). Moreover, using an uncontrolled experimental design, Benowitz et al., *Clin. Pharm. Ther.*, 34, 604 (1983), found that intravenous cotinine produced no cardiovascular changes and only slight differences in various subjective ratings which were comparable to placebo-induced changes found in other experiments with nicotine. Consequently, Benowitz and his colleagues concluded that cotinine lacked significant pharmacologic activity in humans.

ADMINISTRATION AND DOSAGES

While it is possible that, for use in therapy, cotinine and/or its pharmaceutically acceptable salts thereof may be administered as the pure chemicals, as by inhalation of a fine power via an insufflator, it is preferable to present the active ingredient as a pharmaceutical formulation. The invention thus further provides a pharmaceutical formulation comprising cotinine and/or a pharmaceutically acceptable salt thereof, together with one or more pharmaceutically acceptable carriers therefore and, optionally, other therapeutic and/or prophylactic ingredients. The carrier(s) must be acceptable, in the sense of being compatible with the other ingredients of the formulation and not deleterious to the recipient thereof.

Pharmaceutical formulations include those suitable for oral or parenteral (including intramuscular, subcutaneous and intravenous) administration. Forms suitable for parenteral administration also include forms suitable for administration by inhalation or insufflation or for nasal, or topical (including buccal, rectal, vaginal and sublingual) administration. The formulations may, where appropriate, be conveniently presented in discrete unit dosage forms and may be prepared by any of the methods well known in the art of pharmacy. Such methods include the step of bringing into association the active compound with liquid carriers, solid matrices, semi-solid carriers, finely divided solid carriers or combinations thereof, and then, if necessary, shaping the product into the desired delivery system.

Pharmaceutical formulations suitable for oral administration may be presented as discrete unit dosage forms such as hard or soft gelatin capsules, cachets or tablets each containing a predetermined amount of the active ingredient, as a power or as granules; as a solution, a suspension or as an emulsion; or in a chewable base such as a synthetic resin or chicle for ingestion of the cotinine from a chewing gum. The active ingredient may also be presented as a bolus, electuary or paste. Tablets and capsules for oral administration may contain conventional excipients such as binding agents, fillers, lubricants, disintegrants, or wetting agents. The tablets may be coated according to methods well known in the art, i.e., with enteric coatings.

Oral liquid preparations may be in the form of, for example, aqueous or oily suspensions, solutions, emulsions, syrups or elixirs, or may be presented as a dry product for constitution with water or other suitable vehicle before use. Such liquid preparations may contain conventional additives such as suspending agents, emulsifying agents, non-aqueous vehicles (which may including edible oils), or preservatives.

The compounds according to the invention may also be formulated for parenteral administration (e.g., by injection, for example, bolus injection or continuous infusion) and may be presented in unit dose form in ampules, prefilled syringes, small column infusion containers or in multi-dose containers with an added preservative. The compositions may take such forms as suspensions, solutions, or emulsions in oily or aqueous vehicles, and may contain formulatory agents such as suspending, stabilizing and/or dispersing agents. Alternatively, the active ingredient may be in powder form, obtained by aseptic isolation of sterile solid or by lyophilization from solution, for constitution with a suitable vehicle e.g., sterile, pyrogen-free water, before use.

For topical administration to the spidermis, the cotinine may be formulated as ointments, creams or lotions, or as the active ingredient of a transdermal patch. Suitable transdermal delivery systems are disclosed, for example, in A. Fisher et al. (U.S. Pat. No. 4,788,603), or R. Bawa et al. (U.S. Pat. Nos. 4,931,279, 4,668,506 and 4,713,224). Ointments and creams may, for example, be formulated with an aqueous or oily base with the addition of suitable thickening and/or gelling agents. Lotions may be formulated with an aqueous or oily base and will in general also contain one or more emulsifying agents, stabilizing agents, dispersing agents, suspending agents, thickening agents, or coloring agents. The active ingredient can also be delivered via iontophoresis, e.g., as disclosed in U.S. Pat. Nos. 4,140,122, 4,383,529, or 4,051,842.

Formulations suitable for topical administration in the mouth include unit dosage forms such as lozenges comprising active ingredient in a flavored base, usually sucrose and acadia or tragacanth; pastilles comprising the active ingredient in an inert base such as gelatin and glycerin or sucrose and acacia; mucoadherent gels, and mouthwashes comprising the active ingredient in a suitable liquid carrier.

When desired, the above-described formulations can be adapted to give sustained release of the active ingredient employed, e.g., by combination with certain hydrophilic polymer matrices, e.g., comprising natural gels, synthetic polymer gels or mixtures thereof. Pharmaceutical formulations suitable for rectal administration wherein the carrier is a solid are most preferably presented as unit dose suppositories. Suitable carriers include cocoa butter and other materials commonly used in the art, and the suppositories may be conveniently formed by admixture of the active compound with the softened or melted carrier(s) followed by chilling and shaping in molds.

Formulations suitable for vaginal administration may be presented as pessaries, tampons, creams, gels, pastes, foams or sprays containing, in addition to the active ingredient, such carriers as are known to the art to be appropriate.

For administration by inhalation, the compounds according to the invention are conveniently delivered from an insufflator, neubilzer or a pressurized pack or other convenient means of delivering an aerosol spray. Pressurized packs may comprise a suitable propellant such as dichlorotetrafluoroethane, trichlorofluoromethane, dichlorotetrafluoroethane, carbon dioxide or other suitable gas. In the case of a pressurized aerosol, the dosage unit may be determined by providing a valve to deliver a metered amount.

Alternatively, for administration by inhalation or insufflation, the compounds according to the invention may take the form of a dry power composition, for example, a powder mix of the compound and a suitable powder base such as lactose or starch. The powder composition may be presented in a unit dosage form in, for example, capsules or cartridges or, e.g., gelatin or blister packs from which the powder may be administered with the aid of an inhalator or insufflator.

For intranasal administration, the compounds of the invention may be administered via a liquid spray, such as via a plastic bottle atomizer. Typical of these are the Mistometer a (Wintropo) and the Medihaler a (Riker). For topical administration to the eye, the cotinine can be administered as drops, gels (see, S. Chrai et al., U.S. Pat. No. 4,255,415), gums (see, S. L. Lin et al., U.S. Pat. No. 4,136,177) or via a prolonged-release ocular insert (see, A. S. Michaels, U.S. Pat. No. 3,867,519 and H. M. Haddad et al., U.S. Pat. No. 3,870,791).

The pharmaceutical compositions according to the invention may also contain other adjuvants such as flavorings, colorings, antimicrobial agents, or preservatives.

It will be further appreciated that the amount of cotinine, or an active salt or derivative thereof, required for use in treatment will vary not only with the particular salt selected but also with the route of administration, the nature of the condition being treated and the age and condition of the patient and will be ultimately at the discretion of the attendant physician or clinician.

In general, however, a suitable dose will be in the range of from about 1 to about 200 mg/kg, e.g., from about 10 to about 150 mg/kg of body weight per day, such as 3 to about 75 mg per kilogram body weight of the recipient per day, preferably in the range of 6 to 135 mg/kg/day, most preferably in the range of 15 to 90 mg/kg/day, calculated as (−)-cotinine in the free base form.

The compound is conveniently administered in unit dosage form; for example, containing 5 to 2000 mg, conveniently 10 to 1500 mg, most conveniently, 50 to 1000 mg of active ingredient per unit dosage form.

Ideally, the active ingredient should be administered to achieve peak plasma concentrations of the active compound of from about 0.5 to about 100 pM, preferably, about 1 to 75 pM, most preferably, about 2 to about 50 pM. This may be achieved, for example, by the intravenous injection of a 0.05 to 10% solution of the active ingredient, optionally in saline, or orally administered as a bolus containing about 1–200 mg of the active ingredient.

Desirable blood levels may be maintained by continuous infusion to provide about 0.01–10.0 mg/kg/hr or by intermittent infusions containing about 0.4–30 mg/kg of the active ingredient(s). The desired dose may conveniently be presented in a single dose or as divided doses administered at appropriate intervals, for example, as two, three, four or more sub-doses per day. The sub-dose itself may be further divided, e.g., into a number of discrete loosely spaced administrations; such as multiple inhalations from an insufflator or by application of a plurality of drops into the eye. The invention will be further described by reference to the following detailed example.

EXAMPLE I

Intravenous Administration of (−)-Cotinine

A. Subjects: Participants included 18 healthy male volunteers between the ages of 18 and 40 years old who had 1)

no history of psychiatric, alcohol and drug abuse disorders, 2) smoked at least one pack of cigarettes per day for one year prior to study admission, 3) an expired-air carbon monoxide concentration of greater than 20 ppm, 4) not currently on any medication, and 5) not donated blood in the past 90 days. Potential subjects were carefully screened for physical and mental health problems.

B. Drug Preparation and Administration Procedures: (−)-Cotinine base was synthesized from (−)-nicotine using the bromine-zinc oxidation method described by E. R. Bowman et al., *Biochem. Preparations*, 10, 36 (1963). Hereinafter, the term "cotinine" will be used to refer to (−)-cotinine. The cotinine base was analyzed for impurities using gas chromatography/mass spectrometry and thin layer chromatography and was found to be pure. Using sterile techniques, cotinine solution was prepared for intravenous administration. Cotinine base was combined with sterile normal saline solution to achieve a concentration of three mg of cotinine base per one ml of solution. This solution was autoclaved and found to be non-pyrogenic using a standard Limulus pyrogenicity testing techniques. The cotinine solution was again tested for molecular structural integrity and concentration accuracy using GC/MS. Next, 10 ml of cotinine solution (30 mg cotinine) were placed into 20 ml injection vials, sealed and stored in a refrigerator until used. The placebo was ten ml of sterile normal saline solution. Placebo and active drug vials were prepared and labeled in a double-blind manner by pharmacy personnel. In addition to pharmacy personnel, one study physician who had no contact with subjects during the experimental sessions had access to the drug code in the event of a medical emergency. During sessions, subjects received 10 ml (30 mg) of cotinine base solution diluted to 15 ml with sterile normal saline solution or placebo (15 ml of sterile saline solution) infused intravenously through a 20 gauge indwelling intravenous catheter. This infusion rate was chosen so as not to exceed two mg per minute of cotinine delivered to the subject. Infusions were performed using a controlled rate syringe infusion pump. All subjects received cotinine and placebo infusions using a randomly-assigned double-blind counterbalanced order design.

C. Dependent Measures: The physiological parameters monitored included heart rate, systolic, diastolic and mean arterial blood pressure, and a 12-lead electrocardiogram (ECG) with measurement of PR, QRS and QT intervals. The biochemical parameters included expired-air carbon monoxide level (CO), serum nicotine and cotinine concentrations. Carbon monoxide was measured using standard techniques. The serum nicotine and cotinine concentration assays were performed using gas chromatography and mass spectrometry at the Laboratory of Physiological Hygiene at the University of Minnesota Medical School.

Self-reported ratings of subjective state, mood and cigarette withdrawal symptomswere obtained from the subjects. These measures included the Profile of Mood States questionnaire (POMS), several 100 mm visual analog scales (VAS) and the cigarette withdrawal symptoms checklist syndrome (J. R. Hughes, et al., *Archives of General Psychology*, 43, 289, (1986)). The Record of Withdrawal Symptom is a 0=(none) to 5=(severe) scale of 12 symptoms associated with TWS: craving, irritable/angry, anxious/tense, difficulty concentrating, restless, impatient, excessive hunger, insomnia, increased eating, drowsiness, headaches and miscellaneous group including tremor, heart racing, sweating, dizzy or g.i. problems.

Two VAS forms were used. One with 11 adjectives including "Pleasant", "Need for Cigarettes", "Energy", "Hungry", "Down", "Sedated", "Anxious", "Stimulated", "Fatigue", "Craving for Cigarettes" and a separate VAS for "Craving for Tobacco". Also, an adverse effects questionnaire (AEQ) was used to assess possible problems associated with cotinine administration. These problems were restlessness, headaches, tachycardia/palpitations, tremor, excessive seating, nausea/vomiting, upset stomach, lightheadedness/dizzy, drowsy, irritable, and excessive salivation. The symptoms assessed were those known to be experienced following nicotine administration.

D. Procedure: This study was performed on an outpatient basis over nine days. Subjects were required to attend five sessions. All sessions were held at the Tobacco Research Laboratory associated with the University of Minnesota Hospital Complex, Minneapolis, Minn. The first session was used to obtain informed consent, physical and psychological screening of the prospective participant, background and baseline data collection. Also, the subject was allowed to habituate to the data collection procedures to be utilized during the sessions. If the participant met inclusion criteria, the participant was scheduled for his next visit. Prior to session 2, the subject was randomly-assigned to one of the two during administration order conditions.

Sessions 2 and 4 were used for baseline measurement of all variables under conditions of ad libitum cigarette smoking. These sessions occurred between 5 and 7 PM, and lasted about 15 minutes. Vital signs, CO, WSC, VAS, POMS and AEQ were completed. Also, blood was drawn for later measurement of serum nicotine and cotinine concentration. Sessions 2 and 4 were held seven days apart and began at the same time as sessions 3 and 5. After departing the laboratory, the subjects were required to refrain from cigarette smoking and other forms of tobacco use over the 48 hours following sessions 2 and 4 and prior to sessions 3 and 5, at which time they were to report back to the laboratory for their drug infusion during sessions 3 and 5.

During sessions 3 and 5, subjects received cotinine or placebo infusions in a counterbalanced order. Sessions 3 and 5 were held 48 hours after sessions 2 and 4 during which time the subject was tobacco abstinent. After the subject reported to the laboratory, baseline measurements of CO, vital signs, WSC, VAS, POMS and AEQ were made. Next, the ECG electrodes were attached to the chest wall and limbs. For intravenous drug administration and access in the event of an adverse event, a 20 gauge indwelling catheter was placed in a prominent vein in the non-dominant forearm. This allowed the subject to freely complete subjective effects questionnaries during the remainder of the session. Heart rate and blood pressure were recorded. Using standard venipuncture techniques, five mls of blood were drawn from the antecubital area of the dominant arm for later serum nicotine and cotinine concentration analyses. At intervals 5, 15, 30, 60 and 120 minutes after the drug infusion, the subject's heart rate, blood pressure, ECG, WSC, VAS, and AEQ were measured, and blood was drawn. Also, the POMS was completed at 30, 60 and 120 minutes after drug administration.

E. Statistical Analyses:All questionnaires were scored and the data was entered into a computer by a research assistant. At the end of the experiment and when all data scoring, collation and entry were completed, the drug code and serum cotinine concentrations were entered into the computer. For the given measures, a two within subject factor (dose by time) repeated measures analysis of variance was performed. For significant interactions, post-hoc analyses using the least significant difference tests were performed. Statistical significance was defined as a p-value equal to or less than −5 probability of a chance occurrence.

F. Results: The participants were healthy 18 male cigarette smokers whose average age was 25.6 years (SD=6.4). None of the participants were interested in cigarette smoking cessation. They smoked an average of 24.6 (SD=5.5) cigarettes per day. Their average expressed-air carbon monoxide concentration was 27.6 ppm (SD=9.6). The average FTC estimated nicotine yield of their cigarettes was 0.94 (SD=0.3). Their mean education level was 14.8 years (SD=2.2).

Fourteen of eighteen of the participants remained abstinent during the abstinence phases of the experiment. All participants were included in the data analyses. Intravenous cotinine administration had no effect on specific cardiovascular parameters such as heart rate, blood pressure and the electrocardiographic intervals (e.g., PR, QRS and QT). These findings are consistent with previous reports.

The biochemical variables of interest included the serum cotinine and nicotine concentrations. The average baseline serum cotinine concentrations for session 2 was 378 ng/ml (SE=43). During the cotinine session, the serum cotinine concentration increased from 73 ng/ml (SE=17) prior to the session to 513 ng/ml (SE=37; p<0.001) at the end of the session. During the placebo session, the serum cotinine concentration decreased from 85 ng/ml (SE=19) prior to the session 77 ng/ml (SE=20) at the end of the session. More importantly, the serum nicotine concentration showed no significant change during the session which rules out the possibility of unanticipated nicotine administration as the factor responsible for the reported effects in this experiment.

In Table 1, the significant subjective changes are listed. Cotinine was found to significantly decrease self-reported ratings of sedation during the session, while insomnia and vigor (.e., ratings of stimulated minus sedated). Also, there was a nearly significant tendency for cotinine to increase feelings of anxiety and tenseness, while decreasing pleasant feelings.

In Table 2, the various measures of appetite are presented. The repeated measures analysis of variance showed a trend towards significance, however was not significant. 14 of 18 participants showed a minimal to large cotinine effect as an appetite suppressant using the self-reported measures of hunger (Sign test; p<0.05). As a result, a two within subject factor repeated measures analysis of variance was performed. The subjects reported feeling significantly less hungry during the cotinine session when compared to placebo (p<0.001) within these 14 subjects. While no significant difference was found for ratings of excessive hunger, the trend was the same in these individuals. No difference was observed for increased eating. The average hunger score was derived by using the weighted average of excessive hunger (excessive hunger×20) added to the rating of hunger. The average hunger rating was significantly decreased during the cotinine condition as opposed to placebo (p<0.02).

TABLE 1

| Variable | 0 min Mean (SE) | 5 min Mean (SE) | 15 min Mean (SE) | 30 min Mean (SE) | 60 min Mean (SE) | Dose p-value | Time p-value | Dose Time p-value |
|---|---|---|---|---|---|---|---|---|
| SEDATED | | | | | | | | |
| Cotinine | 24 (5) | 28 (5) | 28 (5) | 28 (5) | 27 (4) | .03 | .07 | ns |
| Placebo | 26 (3) | 31 (5) | 40 (6) | 36 (6) | 36 (5) | | | |
| RESTLESS (WSC) | | | | | | | | |
| Cotinine | 2.6 (.3) | 1.3 (.3) | 1.3 (.3) | 1.3 (.3) | 1.5 (.3) | .05 | .01 | ns |
| Placebo | 2.5 (.3) | 0.9 (.2) | 0.7 (.2) | 0.8 (.2) | 0.8 (.2) | | | |
| RESTLESSNESS (AEQ) | | | | | | | | |
| Cotinine | 1.8 (.2) | 1.2 (.1) | 1.2 (.1) | 1.4 (.1) | 1.4 (.2) | .05 | .001 | ns |
| Placebo | 1.9 (.2) | 1.0 (.0) | 1.0 (.0) | 1.1 (.1) | 1.0 (.0) | | | |
| INSOMNIA | | | | | | | | |
| Cotinine | 1.1 (.3) | 0.2 (.1) | 0.1 (.1) | 0.1 (.1) | 0.1 (.1) | .02 | .01 | .02 |
| Placebo | 0.5 (.3) | 0.1 (.1) | 0.0 (0) | 0.0 (0) | 0.0 (0) | | | |
| VIGOR | | | | | | | | |
| Cotinine | 29 (8) | 23 (5) | 21 (5) | 17 (4) | 20 (6) | .05 | .01 | ns |
| Placebo | 30 (6) | 20 (8) | 5 (6) | 8 (6) | 2 (5) | | | |
| PLEASANT | | | | | | | | |
| Cotinine | 41 (3) | 50 (3) | 47 (3) | 47 (4) | 46 (4) | .08 | ns | ns |
| Placebo | 42 (3) | 53 (3) | 55 (4) | 51 (3) | 52 (4) | | | |
| ANXIOUS/TENSE | | | | | | | | |
| Cotinine | 2.8 (.4) | 1.9 (.3) | 1.5 (.3) | 1.4 (.3) | 1.7 (.3) | .07 | .01 | ns |

TABLE 1-continued

| | DEPENDENT MEASURES | | | | | | | |
|---|---|---|---|---|---|---|---|---|
| Variable | 0 min Mean (SE) | 5 min Mean (SE) | 15 min Mean (SE) | 30 min Mean (SE) | 60 min Mean (SE) | Dose p-value | Time p-value | Dose Time p-value |
| Placebo | 2.8 (.3) | 1.2 (.2) | 1.1 (.3) | 1.1 (.2) | 0.9 (.2) | | | | ns = non-significant

TABLE 2

| | HUNGER SCORES | | | | | | | |
|---|---|---|---|---|---|---|---|---|
| Variable | 0 min Mean (SE) | 5 min Mean (SE) | 15 min Mean (SE) | 30 min Mean (SE) | 60 min Mean (SE) | Dose p-value | Time p-value | Dose Time p-value |
| HUNGRY | | | | | | | | |
| Cotinine | 34 (5) | 27 (5) | 21 (3) | 26 (5) | 35 (6) | .001 | .06 | ns |
| Placebo | 42 (6) | 36 (6) | 41 (8) | 39 (6) | 43 (6) | | | |
| EXCESSIVE HUNGER | | | | | | | | |
| Cotinine | 0.8 (.2) | 0.3 (.1) | 0.5 (.2) | 0.6 (.2) | 1.0 (.3) | ns | .03 | ns |
| Placebo | 1.2 (.4) | 0.7 (.3) | 0.6 (.3) | 0.9 (.4) | 1.2 (.4) | | | |
| INCREASED EATING | | | | | | | | |
| Cotinine | 1.4 (.3) | 0.2 (.1) | 0.2 (.2) | 0.3 (.2) | 0.3 (.2) | ns | .001 | ns |
| Placebo | 1.1 (4) | 0.2 (.1) | 0.2 (.1) | 0.1 (.1) | 0.2 (.1) | | | |
| AVERAGE HUNGER SCORE | | | | | | | | |
| Cotinine | 47 (9) | 33 (6) | 31 (7) | 39 (9) | 55 (11) | .02 | .007 | ns |
| Placebo | 67 (11) | 50 (10) | 54 (10) | 57 (13) | 87 (13) | | | | ns = non-significant

G. Discussion: The purpose of the study was to determine whether intravenously administered (−)-cotinine base has significant pharmacologic activity in nicotine experienced individuals. The data presented herein is the first demonstration that cotinine is a pharmacologically active compound which produced subjective changes including decreases in self-reported ratings of hunger in humans without significantly affecting cardiovascular activity.

The findings reported herein suggest that cotinine may serve to as an appetite suppressant and could be responsible in part for the decreased body weight of tobacco users. The data suggest that cotinine is a psychomotor stimulant and its ability to suppress appetite probably stems from this activity. Acutely, psychomotor stimulants typically make people feel more anxious, irritable, restless and impatient until they become tolerant to these effects. Also, psychomotor stimulants typically are used as appetite suppressants (e.g., phentermine, phenmetrazine, emphetamine, fenfluramine, diethylproprion). Nicotine has been shown to increase resting metabolism and decrease perceived taste intensity of various foods in nicotine-experienced and nicotine-naive individuals suggesting a mechanism by which this drug exerts its effects. If nicotine and cotinine act through the same mechanism, then cotinine should act similarly in nicotine-experienced, nicotine-abstinent and/or nicotine-naive individuals.

All publications and patent applications mentioned in this specification are indicative of the level of ordinary skill in the art to which this invention pertains. All publications and patent applications are herein incorporated by reference to the same extend as if each individual publication or patent application was specifically and individually indicated to be incorporated by reference.

In summary, using a randomized double-blind placebo-controlled counterbalanced-order design intravenous cotinine was administered to nicotine-experienced tobacco users. Cotinine is pharmacologically-active and produced subjective changes including decreases self-reported ratings of hunger consistent with psychomotor stimulant activity without significantly affecting cardiovascular activity. As a result, cotinine serves to act as an appetite suppressant which can reduce body weight in nicotine-experienced, nicotine-abstinent and/or nicotine-naive humans.

It will be apparent to one of ordinary skill in the art that many changes and modifications can be made in the invention without departing from the spirit or scope of the appended claims.

I claim:

1. A therapeutic method to control long-term human body weight in a nicotine-naive human comprising: administering an amount of cotinine or a pharmaceutically acceptable salt thereof to a human in need of such treatment.

2. The method of claim 1 wherein: the cotinine is (−)-cotinine.

3. The method of claim 1 wherein: the cotinine is a salt of (−)-cotinine.

4. The method of claim 1 wherein: the cotinine or the pharmaceutically acceptable salt thereof is administered orally.

5. The method of claim 1 wherein: the cotinine or the pharmaceutically acceptable salt thereof is orally administered by means of a gum preparation intended to deliver cotinine through chewing.

6. The method of claim 1 wherein: the cotinine or the pharmaceutically acceptable salt thereof is administered parenterally.

7. The method of claim 1 wherein: the cotinine or the pharmaceutically acceptable salt thereof is administered by means of a transdermal delivery system.

8. The method of claim 1 wherein: the cotinine or the pharmaceutically acceptable salt thereof is administered intraocularly.

9. The method of claim 1 wherein: the cotinine or the pharmaceutically acceptable salt thereof is administered via an intraocular insert.

10. The method of claim 1 wherein: the cotinine or the pharmaceutically acceptable salt thereof is administered intravenously.

11. The method of claim 1 wherein: the cotinine or the pharmaceutically acceptable salt thereof is administered intranasally.

* * * * *